United States Patent [19] [11] 4,058,124
Yen et al. [45] Nov. 15, 1977

[54] DISPOSABLE ABSORBENT ARTICLES CONTAINING PARTICULATE, FREE-FLOWING, INSOLUBLE SWELLABLE POLYMERS

[75] Inventors: Steven N. Yen, Highland Mills; Frederick D. Osterholtz, Warwick, both of N.Y.

[73] Assignee: Union Carbide Corporation, New York, N.Y.

[21] Appl. No.: 563,128

[22] Filed: Mar. 28, 1975

Related U.S. Application Data

[60] Division of Ser. No. 303,880, Nov. 6, 1972, Pat. No. 3,900,378, which is a continuation-in-part of Ser. No. 194,511, Nov. 1, 1971, abandoned.

[51] Int. Cl.$^2$ .................... A61F 13/16; A61F 13/18
[52] U.S. Cl. .......................................... 128/284; 47/9; 47/DIG. 7; 47/DIG. 10; 71/64 C; 71/79; 71/DIG. 1; 128/285; 128/290 R; 204/159.12; 204/159.14; 204/159.16; 204/159.19; 204/159.2; 260/42; 260/42.12; 260/42.17; 260/42.29; 260/42.51; 260/42.53; 260/42.54; 424/79; 424/80; 424/81; 424/82
[58] Field of Search ............... 204/159.12, 159.14, 204/159.16, 159.19; 128/284, 285, 290; 260/42.12, 42.17, 42.29, 42.51, 42.53, 42.54

[56] References Cited

U.S. PATENT DOCUMENTS

| | | | |
|---|---|---|---|
| 3,121,674 | 2/1964 | Guthrie | 204/159.14 |
| 3,264,202 | 8/1966 | King | 204/159.11 |
| 3,316,676 | 5/1967 | Legal, Jr. et al. | 71/DIG. 1 |
| 3,336,129 | 8/1967 | Herrett et al. | 117/93.31 X |
| 3,470,078 | 9/1969 | King | 204/159.14 |
| 3,900,378 | 8/1975 | Yen et al. | 204/159.14 |

Primary Examiner—Richard B. Turer
Attorney, Agent, or Firm—William Raymond Moran

[57] ABSTRACT

Particulate, free-flowing, insoluble swellable polymers are provided which are comprised of a mixture of an insoluble, swellable hydrogel and inert filler. The mixtures are free-flowing powders or granules which can absorb many times their weight of water and hence are useful as a soil amendment.

5 Claims, No Drawings

DISPOSABLE ABSORBENT ARTICLES CONTAINING PARTICULATE, FREE-FLOWING, INSOLUBLE SWELLABLE POLYMERS

This is a division of application Ser. No. 303,880 filed Nov. 6, 1972, now U.S. Pat. No. 3,900,378 issued Aug. 19,1975 which in turn is a continuation-in-part of application Ser. No. 194,511 filed Nov. 1, 1971, now abandoned.

This invention relates in general to free-flowing, swellable, particulate polymeric materials and to a process for their preparation. In one aspect, this invention is directed to blends of swellable hydrogels and inert fillers. In a further aspect, the invention is directed to a plant growth medium.

Prior to the present invention, a variety of formulations and methods have appeared in the literature for modifying plant growth. A wide variety of fertilizers, nutrients, fungicides, insecticides, nematocides, and the like are currently employed for agricultural applications. Of particular interest is a plant growth medium as set forth in U.S. Patent 3,336,129. This medium is comprised preferably of soil and a particulate, water insoluble, cross-linked matrix of polymeric alkylene ether having the ability to reversably sorb and desorb substantial amounts of solutions. Illustrative of the cross-linked polymeric material is poly(ethylene oxide) which has been cross-linked by irradiation.

As indicated in the patent, the preferred method for producing polymeric materials which have the highest water absorptive capacity, is to carry out the irradiation on an aqueous solution of the polymer. After exposure to irradiation a gel-like material is formed, the water removed and a dry residue recovered. The polymeric material can then be subdivided into particles of small size by known processes such as grinding operations.

Although it is indicated in the patent that irradiation of the non-cross-linked polymers can be carried out in the solid phase, this is not preferred. For example, it is known that dry poly(ethylene oxide) degrades when irradiated in dry powder form in the presence of oxygen. However, when irradiated as an aqueous solution crosslinking easily occurs to produce a water absorbing material with little or no degradation. As noted in this patent, the cross-linked material is a gel which must be dehydrated and then ground to a fine particulate form at low temperatures of the order of liquid nitrogen. This of course, adds to the overall time of preparation and cost of the final material. Since a particularly attractive application for the material is a plant growth medium, the overall cost of the material must be kept at a minimum. However, due to the multiplicity of steps involved in the process taught in the patent, this particular application has not been commerically successful.

A further disadvantage encountered in cross-linking aqueous solutions of the polymers, is that they are not readily dispersible in water. The individual particles tend to agglomerate or clump together when their outer surfaces are first wet. Thereafter, the rate of dissolution is very slow and high speed stirring must be employed for lengthy periods of time. U.S. Pat. No. 3,606,093 emphasizes the difficulties in dissolving these polymers and is directed to a device specifically designed to minimize this problem.

Accordingly one or more of the following objects will be achieved by the practice of this invention. It is an object of this invention to provide free-flowing, swellable, particulate polymers and a process for their preparation. Another object is to provide particulate polymers which are comprised of an insoluble swellable hydrogel and an inert filler. A further object of the invention is to provide powders or granules comprised of insoluble poly(ethylene oxide) and inert fillers such as pulverulent wood. Another object of this invention is to provide blends of hydrophilic polymer, water, and inert filler which are free-flowing and have improved blending properties by the presence therein of reagent grade tricalcium phosphate. A still further object is to provide a process for the preparation of these materials wherein the preparation of aqueous solutions of the polymer are avoided. Another object is to provide a process which avoids extensive dehydration of the cross-linked material. These and other objects will readily become apparent to those skilled in the art in the light of the teachings herein set forth.

In its broad aspect the present invention is directed to free-flowing, insoluble swellable hydrophilic polymers in particulate form and to a process for their preparation. The process is comprised of the steps of:

a. blending a mixture of at least one water soluble, pulverulent hydrophilic polymer and at least one pulverulent inert filler, a substantial portion of the filler having a particle size less than that of the polymer and present in an amount sufficient to cover a substantial portion of the surface area of the pulverulent polymer, b. thereafter while said blending is continued, contacting the mixture under thorough agitation with a finely divided spray of water in an amount not to exceed that at which the mixture is maintained as a free-flowing powder to granules, and c. exposing the mixture to ionizing radiation for a period of time to cross-link said polymer.

The particulate materials by the process of this invention are free-flowing, insoluble hydrophilic polymers which are capable of absorbing many times their weight of water or solutions of salt and the like. Moreover, the process avoids many of the disadvantages inherent in prior art procedures. For example, the process does not involve the preparation of an aqueous solution of the polymer with its inherent difficulties and disadvantages. Nor does the process require the removal of as large quantities of water as is the case in prior techniques. Due to solubility and viscosity it is exceedingly difficult, for example, to prepare aqueous solutions containing more than 20 weight percent of higher molecular weight poly(ethylene oxide), such as those having molecular weights in excess of 100,000. The usual solutions contain 4 to 8 weight percent polymer, which when cross-linked provide a rather firm gel. Hence, after cross-linking a rather large amount of water must be removed before the hydrogel can be ground. Additionally, the process avoids the exposure of dry solid polymer to irradiation with its accompanying degradation.

Due to the presence of an inert filler, which coats the polymer, sufficient water can be added to the polymer to effect cross-linking without substantial degradation and yet, due to a coating of the filler, the sticky particles of wet polymer do not agglomerate beyond the stage of being a free-flowing particulate material. The product remains free-flowing at all times and if desired only relatively small amounts of water need be removed. In practice it has been found that the blending process is substantially improved if the filler is first blended with a portion of the water prior to contact with the polymer. Thereafter while the blending process is continued in step (b) above, the remainder of the water is added. However, the water added to the filler should not exceed that at which the filler is maintained in a free-flowing state. The amount of water initially added to the filler will, of course, vary with the nature of the filler. In general up to 50 weight percent and higher, of the total weight of water can be blended with the filler prior to blending the filler and polymer.

As previously indicated, the invention utilized at least one water soluble or hydrophilic polymer. A wide variety of polymers can be employed. the only limitation being that they are capable of cross-linking in the presence of water to form an essentially insoluble gel which can undergo dehydration and hydration reversibly. Illustrative polymers which can be employed include, among others, Poly(ethylene oxide),
Polyvinyl pyrrolidone,
Polyacrylamide,
Anionic polyacrylamide,
Polyvinylalcohol,
Maleic anhydride-vinylether copolymers,
Polyacrylic acid,
Ethylene-maleic anhydride copolymers,
Polyvinylethers,
Dextran,
Gelatin,
Hydroxy propyl cellulose,
Methyl cellulose,
Carboxymethyl cellulose,
Hydroxyethyl-carboxymethyl cellulose
Hydroxyethyl cellulose,
Propyleneglycol alginate,
Sodium alginate,
Polyethyleneimine,
Polyvinyl alkyl pyridinium halides, e.g. polyvinyl-n-butyl-pyridinium bromide,
Polyproline,
Natural starches,
Casein,
Proteins,
Polymethacrylic acid,
Polyvinylsulfonic acid,
Polystyrene sulfonic acid,
Polyvinylamine,
Ammonium polyacrylates,
Hydroxyalkyl acrylates,
Hydroxyalkyl methacrylates,
Hydroxyalkoxyalkyl acrylates,
Hydroxyalkoxyalkyl methacrylates,
Polyethylene oxide adduct esters of acrylic and methacrylic acids,
Alkoxy acrylates and methacrylates,
Alkoxyalkyl acrylates and methacrylates,
Partially hydrolyzed polyacrylamides,
Poly-4-vinylpyridine, polymerized monoesters of olefinic acids, polymerized diesters of olefinic acids, acrylamide and difunctional polymerizable materials, e.g. diacids, diesters or diamides, and the like.

It should be noted that the instant invention is not limited to the use of only one of the materials listed above but includes mixtures of two or more polymers. Additionally, it is also possible to employ copolymers of the aforementioned compounds or materials similar to these. For example, copolymers of ethylene oxide and minor or major amounts of other alkylene oxides can also be used.

In general, a wide variety of animal, vegetable or mineral inert fillers can be employed in the practice of this invention, the only requirement being that the fillers separate the polymeric particles and keep the mixture free-flowing. In practice it has been observed that best results are achieved when a substantial portion of the filler has a particle size which is less than that of the polymer. This insures that the wet polymeric particles are quickly coated with filler and are prevented from sticking to each other. Preferably, at least 50 percent of the filler should be of a particle size smaller than the polymer. In general, the particle size of the polymer will be such that at least about 90 percent of the polymer passes through a 20 mesh screen. In general, about 90 percent of the wet blend particles will be less than about one sixteenth inch in diameter.

Illustrative fillers include, among others, pulverulent wood and wood products, such as wood flours, wood pulp fluff, tree bark, cellulose flocs, cotton linter flocs, and the like; minerals such as perlite, synthetic fillers, such as nylon flocs, rayon flocs, and the like; diatamaceous earth, coal talc, clay, fly ash, coal dust, magnesium silicates, fertilizers, or combinations thereof.

It should be noted, as indicated in the examples, that the ratio of water, filler and polymer are interdependent. In practice it has been observed that when the polymer and filler are present in equal amounts and water added in an amount not to exceed that at which the mixture is maintained in a free-flowing particulate form, it can be essentially completely insolubilized by irradiation. Although equal amounts of polymer and filler are preferred, the ratio can vary widely depending on the particular polymer employed, filler, or desired end use of the product. For example, polymer to filler ratio can be from about 1:9 to about 9:1. A preferred range of filler is from about 40 to about 60 weight percent of the mixture.

It has also been observed that the blend of hydrophilic polymer, water, and the pulverulent inert filler can be made substantially more free-flowing and less agglomerated by substitution of reagent grade tricalcium phosphate, $Ca_3(PO_4)_2$ for at least some of the inert filler. As indicated in Example 57 when all of the wood flour was substituted by reagent grade tricalcium phosphate the material during blending was exceptionally free-flowing and free of agglomeration. The blend had a very dry "feel" and did not compact as easily as blends with the wood flour alone. The use of technical grade tricalcium phosphate in place of all the wood flour did not give satisfactory results. It can however be used in place of some of the wood flour. In order to obtain a useful improvement in blending it has been found that at least 0.5 weight percent of the filler should be substituted with reagent grade or technical grade tricalcium phosphate. Attempts to prepare blends using other calcium salts resulted in no improvement in the physical properties of the blend.

The amount of water added need only be a minimum amount, i.e., that sufficient to enable the polymer to be essentially completely insolubilized by irradiation. As previously indicated the amount should not exceed that at which the mixture is maintained in a free-flowing particulate form. If the product is to be used as an absorbent, it will be desirable to keep the water at a minimum in order to avoid or minimize the need for a dehydration step. In general, the water content can range from about 15 to about 80 weight percent based on the mixture of polymer and filler. For some applications, it may be desirable to have a product with a higher water content, and in some instances this figure can be exceeded.

The particulate, free-flowing, insoluble swellable polymers of this invention in addition to fillers can also contain a wide variety of additives. For instance, various cross-linking enhancers such as methylene-bis-acrylamide, can be added prior to irradiation. Various stabilizers, dispersants, dyes, pigments, diluents and the like can be employed if desired. When the polymeric powders are used as a soil amendment they can be admixed with, or contain wetting agents, surfactants, fertilizers, urea, herbicides, fungicides, nematocides, insecticides, soil conditioning agents, and the like. While most of these would be added after the particulate materials have been prepared, some could be added during the blending stage of the process. For example, if a stabilizer is desired, it can be added to the water which will be sprayed on the mixture.

For example, it has been observed that poly(ethyleneimine) is an excellent stabilizer. These are polymers prepared from ethyleneimine and which contain in a major amount the recurring unit:

and in a minor amount the recurring unit:

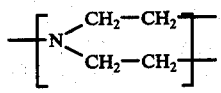

In practice poly(ethyleneimine) polymers having molecular weights of from about 10,000 to about 100,000 are ideally suited for use in the instant invention. Particularly preferred are the poly(ethyleneimine) polymers having molecular weight of from about 20,000 to about 80,000. These polymers are prepared by processes known in the literature and are commercially available.

In practice, the poly(ethyleneimine) stabilizer is employed in a stabilizing amount. By the term "stabilizing amount" as employed throughout the specification and claims, is meant that quantity of poly(ethyleneimine) which when admixed with the polymer will decrease the rate of degradation over that of the unstabilized polymer. It has been observed that as little as about 0.01 weight percent based on the solid polymer, will effectively stabilize the polymer against degradation. A range of from about 0.2 to about 3.0 weight percent is preferred. However, if desired, concentrations of poly(ethyleneimine) as high as 50 weight percent can be employed.

The water-insoluble hydrophilic crosslinked polymers are produced by subjecting the mixture, to sufficient ionizing radiation to crosslink and insolubilize the polymer forming thereby a water-insoluble hydrophilic product. As used herein, the term "ionizing radiation" includes that radiation which has sufficient energy to cause electronic excitation and/or ionization in the polymer molecules but which does not have sufficient energy to affect the nuclei of the constituent atoms. Convenient sources of suitable ionizing radiation are gamma ray-producing radioactive isotopes such as Co$^{60}$ and Cs$^{137}$, spent nuclear fuel elements, X-rays such as those produced by conventional X-ray machines, and electrons produced by such means as Van de Graaff accelerators, linear electron accelerators, resonance transformers, and the like. Suitable ionizing radiation for use in the present invention will generally have an energy level in the range from about 0.05 MeV to about 20 MeV.

The irradiation of the non-crosslinked (water soluble) polymers can be carried out in the air, in a vacuum, or under various gaseous atmospheres. Any conventional method can be used to bring the polymer into contact with the ionizing radiation. Suitable methods are well known and understood by those skilled in the art.

The water-soluble poly(ethylene oxide) polymers prior to irradiation will usually have a molecular weight such that the reduced viscosity of the polymer will be within the range of from about 0.5 to about 75, and higher, and preferably from about 1 to about 60, or an aqueous viscosity of 25° C. of from about 225 centipoises measured at a 5 weight percent concentration, to about 12,000 centipoises, and higher measured at a 1 weight percent concentration.

The free-flowing, swellable hydrophilic polymers which are prepared by the process of this invention are useful in a wide variety of fields. For example, the materials can contain, or when dried absorb, large quantities of aqueous fluids and hence are useful as absorbing media for disposable absorbent articles, agricultural applications, such as moisture retainers, and the like. They are of particular interest as an absorbing media for diapers, or catamenial devices such as sanitary napkins and tampons.

The polymers prepared by the process of this present invention, are particularly useful because they possess the ability to incorporate very large amounts of water in the order of 25 to 1000 times their dry weight. Moreover, in addition to possessing the ability to incorporate large amounts of water, they are insoluble in water irrespective of temperature and will retain liquids, solutions and suspensions. In general, the materials are useful for increasing the absorbency of any known or commercially available disposable article. For example, the hydrogels can be incorporated into diapers of the type disclosed in U.S. Pat. Nos. 2,788,003; 2,860,637; 3,306,293; and 2,667,168. Similarly, they can be incorporated into tampons or sanitary napkins of the type disclosed in U.S. Pat. Nos. 3,121,427; 3,070,095 and the like.

The following examples are illustrative:

EXAMPLE 1

One pound of wood flour, having a mesh size such that no more than 0.5% was retained on a U.S. standard 100 mesh sieve and no more than 4% retained on a 140 mesh sieve, and one pound of poly(ethylene oxide) sold by Union Carbide Corporation under the trademark "POLYOX", grade WSR-301 were placed in a Patterson-Kelly LS16 liquids-solids Vee-shell blender. During about 45 minutes, 1300 ml of water containing 14 ml of a 33% aqueous solution of poly(ethyleneimine) were sprayed into the rotating blender through the hollow spinning shaft with which the blender is supplied. The mixture in the blender absorbed the water and remained free-flowing powder or granules. A small amount of agglomeration to particles 1/16-¼ inch in diameter occurred.

The granular material so produced was placed on a moving conveyor belt and passed through a beam of 1.5 million volt electrons from a Van de Graaff electron accelerator. The dose absorbed in the material was approximately 0.25 Megarads. The irradiated powder was allowed to dry by standing at room temperature. When dry, 83% of the resultant powder was not soluble in a 90/10 methanol/water mixture, and the dry powder absorbed 16–25 times its own weight when swollen in water.

Other samples of material from the same blender batch were irradiated to doses from 0.1 to 1.0 Megarads. The insoluble fraction ranged from 74% to 83.7%; the water absorption capacity ranged from 12.8 to 22 times the dry weight.

The 0.25 Megarad sample was used in tomato growth experiments. Tomato seeds were germinated and grown in sand or sand containing 0.25% of the above composition.

In tests where both types received the same amount of water and nutrient, the tomatoes grown in sand plus hydrogel were twice as big as the others after two months. In experiments where all pots were kept at constant water content, the plants in the sand/hydrogel mix used 15–40% less water and were 25% bigger.

EXAMPLE 2

The material prepared in Example 1 was irradiated in sealed containers in a nitrogen atmosphere. At the same dose, higher insolubles content was obtained as indicated in Table I below:

Table I

| Dose (Megarads) | Gel Fraction (Insoluble Fraction of POLYOX) | |
|---|---|---|
| | Irradiation Air | Irradiation $N_2$ |
| .1 | 54.1 | 78.1 |
| .2 | 58.3 | 85.1 |
| .3 | 83.7 | 85.7 |
| .6 | 76.8 | 88.0 |
| 1.0 | 65.2 | 92.1 |

Thus, irradiation in the substantial absence of oxygen gave higher insoluble fractions, that is, higher cross-linking yields.

Where "insoluble fraction" is referred to, it includes the filler. Where "gel fraction" or "insoluble fraction of POLYOX" is referred to, the filler content (usually 50%) has been subtracted, and the "gel fraction" or "insoluble fraction of the POLYOX" is the portion of the originally soluble POLYOX which has become insoluble.

EXAMPLE 3

The same procedure was employed as in the previous example, except that 1.5 pounds polyvinyl alcohol and 1.5 pounds of wood flour were blended with 4.35 pounds of water. After irradiation to doses from 0.1 to 1.0 Mengarads, the samples showed water absorption capacities from 3 to 18 times their dry weight.

EXAMPLE 4–39

In a manner similar to that employed in Example 1, poly(ethylene oxide) was blended with a variety of other fillers. All blends were made in a Patterson-Kelley LS 16 V shell blender. About 30 minutes were required for adding the water. Poly(ethylene oxide) grade WSR-301 was used unless otherwise noted.

Poly(ethyleneimine) type 1000 sold by Dow Chemical Company was added during blending as a 33% aqueous solution in an amount equivalent to 1% of the poly(ethylene oxide) unless otherwise noted. Irradiations were with 1.5 MeV electrons unless noted. In example 3, methylene-bis-acrylamide was added in an amount equivalent to 2% of the poly(ethylene oxide). Solka Floc is a commercially available cellulose pulp floc produced by Brown & Company. In example 16, irradiation was done under a nitrogen atmosphere. Coagulant grade poly(ethylene oxide) was used in example 18, and hydroxy ethyl cellulose in example 19. Polyvinyl alcohol was used in examples 23, 24 and 36. Examples 26 and 29–31 were not considered to be successful since too litter water was used. In example 27 only the 5 mrad was considered successful whereas in example 28 only the 0.5 mrad failed. Example 37 contained 2% urea and example 38 contained 10% starch based on the weight of polymer. Example 39 employed ammonium polyacrylate and demonstrates the use of a polyelectrolyte. The fillers employed and the results obtained are set forth in Table II below:

Table II

POLYOX-Filler-Water Blends

| Ex. No. | POLYOX Pounds | Filler Pounds | Filler Type | Water Pounds | P/F/W Ratio | Dose Range Mrads | Water Capacity Range Based on Total wt. | Gel Content Range, % |
|---|---|---|---|---|---|---|---|---|
| 4 | 2.15 | 0.85 | Solka Floc™ | 2.0 | 1/0.4/0.93 | 0.01–0.8 | 21–37 | 0–73% |
| 5 | 1.5 | 1.5 | Pulp Floc | 4.4 | 1/1/2.9 | 0.1–0.95 | 13–46 | 0–86 |
| 6 | 1.5 | 1.5 | Fir Flour | 4.4 | 1/1/2.9 | 0.1–0.95 | 11–31 | 24–84 |
| 7 | 0.5 | 1.0 | Fir Flour | 3.8 | 1/2/7.5 | 0.1 to 1.0 | | |
| 8 | 0.5 | 1.0 | Fir Flour | 2.5 | 1/2/4.9 | " | 10–20 | 54–81 |
| 9 | 1.0 | 1.0 | Fir Flour | 2.9 | 1/1/2.9 | " | 13–22 | 48–84% |
| 10 | 1.5 | 1.5 | Fir Flour | 4.4 | 1/1/2.9 | 0.25 | 25 | 55% |
| 11 | 1.5 | 1.5 | Fir Flour | 4.4 | 1/1/2.9 | 0.2–0.8 | 16–20 | 59–82% |
| 12 | 1 | 1.0 | Wood Pulp Fluff | 3.1 | 1/1/3.1 | 0.2–0.6 | 16–22 | 54–72 |
| 13 | 1.5 | 1.5 | Fir Flour | 4.4 | 1/1/2.94 | 0.1–0.6 | 17–25 | 39–72% |
| 14 | 1.5 | 1.5 | Solka Floc™ BW 100 | 4.4 | 1/1/2.9 | 0.1 to 0.6 | 20–31 | 3–71% |
| 15 | 1.0 | 0.38 | Wood Pulp Fluff | 3.2 | 1/.38/3.2 | 0.1–0.6 | 26–28 | 36–63 |
| 16 | 1.5 | 1.5 | Fir Flour | 4.4 | 1/1/2.9 | 0.01–0.3 | 19–35 | 29–79 |
| 17 | 1.5 | 1.5 | Fir Flour | 4.4 | 1/1/2.9 | .25 | 24 | |
| 18 | 1.5 | 1.5 | Pulp Floc | 9.0 | 1/1/5.9 | 0.08–1.0 | 13–25 | 36–88 |
| 19 | 1.5 HEC | 1.5 | Fir Flour | 9.0 | 1/1/5.9 | 0.1 to 2.0 | 6–12 | 82–85 |
| 20 | 1 | 1 | Cotton Linters Floc | 3.2 | 1/1/3.2 | 0.1–0.6 | 15–23 | 20–68 |
| 21 | 1.5 | 0.5 | Cotton Linters Floc | 4.5 | 1/0.3/2.95 | 0.1–0.6 | 22–36 | 29–74 |
| 22 | 0.5 | 1.5 | Cotton Linters | 3.8 | 1/3/7.5 | 0.1–0.6 | 10–13 | 12–72 |
| 23 | 1.5 PVA | 1.5 | Wood Flour | 4.6 | | failed | too much water | |
| 24 | 1.5 PVA | 1.5 | Wood Flour | 4.4 | 1/1/2.9 | .1–1.0 | 3–4 | |
| 25 | 1.5 (301) | 1.5 | Wood Flour | 5.1 | 1/1/3.4 | .1–1.0 | 3–18 | 46% gel |

Table II-continued
POLYOX-Filler-Water Blends

| Ex. No. | POLYOX Pounds | Filler Pounds | Filler Type | Water Pounds | P/F/W Ratio | Dose Range Mrads | Water Capacity Range Based on Total wt. | Insoluble Cotent of Total %[1] |
|---|---|---|---|---|---|---|---|---|
| 26 | 1.5 | 1.5 | Eastern White Pine Flour | .15 | 1/1/0.1 | 0.5 to 5.0 | 4.3 to 5.0 | 42–44 |
| 27 | 1.5 | 1.5 | " | .3 | 1/1/0.2 | 0.5 to 5.0 | 5.2 to 5.8 | 44–50 |
| 28 | 1.5 | 1.5 | " | .45 | 1/1/0.3 | 0.5 to 5.0 | 5.3 to 7.2 | 49–53 |
| 29 | .3 | 2.7 | " | .15 | 1/9/0.5 | 0.5 to 5.0 | 5.8 to 6.2 | 80–83 |
| 30 | .3 | 2.7 | " | .3 | 1/9/1 | 0.5 to 5.0 | 5.2 to 5.8 | 79–83 |
| 31 | .3 | 2.7 | " | .45 | 1/9/1.5 | 0.5 to 5.0 | 6.1 to 6.5 | 80–82 |
| 32 | .3 | 2.7 | " | 3.5 | 1/9/11.5 | 0.5 to 5.0 | 7.7 to 9.7 | 87–91 |
| 33 | .3 | 2.7 | " | 4.4 | 1/9/14.7 | 0.5 to 5.0 | 7.9 to 9.8 | 89–90 |
| 34 | 2.7 | .3 | " | .88 | 1/0.11/.33 | 0.5 to 5.0 | 6.4 to 8.8 | 23–28 |
| 35 | 2.7 | .3 | " | 2.0 | 1/0.11/.74 | 0.5 to 5.0 | 12.9 to 15.7 | 46–56 |
| 36 | 1.5 PVA | 1.5 | Wood Flour | 4.4 | 1/1/2.9 | 0.5 to 5.0 | 4.3 to 9.4 | 49–90[2] |
| 37 | 1.5 | 1.5 | Wood Flour | 5.1 | 1/1/3.4 | 0.5–5.0 | 12.8–21 | 80–90 |
| 38 | 1.5 | 1.5 | Wood Flour | 4.4 | 1/1/2.9 | 0.5–5.0 | 14–20 | 80–88 |
| 39 | 1.0 APA | 1.0 | Wood Flour | 2.9 | 1/1/2.9 | 0.5–5.0 | 17 to 97 or more | 90 |

[1] In example 26–39 the insoluble content of total was used in place of gel content range.
[2] In example 36 the insoluble content was measured in pure water rather than a methanol-water mixture.

EXAMPLE 40

The fillers employed and the results obtained are set forth in Table III below:

Table III
POLYOX-Filler-Water Blends

| Example | POLYOX Pounds | Filler Pounds | Filler Type | Water Pounds | F/F/W Ratio | Dose Range Megarads | Water Capacity Range Based on Total wt. | Gel Content Range |
|---|---|---|---|---|---|---|---|---|
| 41 | 9 | 9 | Fir Flour | 26.5 | 1/1/2.95 | 0.1–0.5 | 17–23 | 46–70 |
| 42 | 9 | 9 | Solka Floc SW 40 | 26.5 | 1/1/2.95 | 0.1–0.6 | 24–27 | 26–69 |
| 43 | 9 | 9 | Fir Flour | 26.5 | 1/1/2.95 | Failed - | Water added too fast | |
| 44 | 18 | 18 | Fir Flour | 48.5 | 1/1/2.7 | .25 | 24 | |
| 45 | 18 | 6 3 | Pulp Floc Solka Floc | 48 | 1/0.5/2.65 | Failed - | Too much water | |
| 46 | 9 | 9 | Pulp Floc | 26.5 | 1/1/2.94 | .15–.25 | 23–24 | 47–62 |
| 47 | 7.5 | 7.5 | Pulp Floc | 26.5 | 1/1/3.54 | .1–.2 | 21–24 | 45–63 |
| 48 | 9 | 9 4 | Pulp Floc | 9+15+16 | 1/1.45/3.4 | .1–.2 | 20 | 34–60 |
| 49 | 9 | 9 | Celite 110 | 21 | 1/1/2.33 | .1–1.0 | 4–26 | 25–57 |
| 50 | 10 | 10 | Fir Flour | 26 | 1/1/2.6 | .25 | 21 | 50% |
| 51 | 15 | 15 | Fir Flour | 41 | 1/1/2.75 | Failed - Load too large for blender. | | |
| 52 | 10 | 10 2 | Eastern White Celite | 31 | 1/1.2/3.1 | .25–.3 | 21–23 | 50–54 |
| 53 | 10 | 10 | Wood Flour | 26 | 1/1/2.6 | .25 | 21 | 36% |

Nine pounds of poly(ethylene oxide) WSR-301 and nine pounds of Fir Flour were placed in a Littleford Lodge model FM 130 blender equipped with rotating mixers and the optional high speed "chopper". To this was added in about 30 minutes through a spray nozzle 26.5 pounds of water containing approximately 50 g. polyethylene imine. The granular mixture was irradiated at doses ranging from 0.1 to 0.5 Megarads to give material with insolubles content from 46 to 70% and water absorption capacity of 17 to 21 times its dry weight.

EXAMPLE 41–53

In a manner similar to the preceeding example, larger blends were prepared. All samples were prepared in a Littleford Lodge model FM 130 blender. Time required for water addition was approximately 10–20 minutes. Unless noted otherwise, 1% polyethylene imine based on the poly(ethylene oxide) was added. Poly(ethylene oxide) was WSR-301 unless noted. All samples were irradiated with 1.5 MeV electrons. In example 48, the filler and water were added in stages. example 52 demonstrates the use of mixed fillers.

EXAMPLE 54

Into a Littleford-Lodge Mixer as in example 40 were placed 15 pounds of Douglas Fir wood flour. The blender was started and 7 pounds of water containing 0.8% polyethyleneimine were added and mixed during about 10 minutes. Then 15 pounds of poly(ethylene oxide) WSR-301 were added, blending was resumed, and 30 1/2 more pounds of the water/PEI solution were added. The resulting blend had substantially fewer lumps (agglomerates greater than ¼ to ½ inch in diameter) than typical blends prepared as in example 40.

EXAMPLE 55

One and one half pounds of Douglas Fir wood flour were put into the Vee-Shell Blender used for Example 1. About 2.2 pounds of water were blended in, then 1.5 pounds of POLYOX WSR-301 were added. Another 2.2 pounds of water were added as blending continued. The resulting blend had substantially fewer lumps (agglomerates greater than ¼ to ½ inch in diameter) than a typical blend prepared as in example 1.

EXAMPLE 56

A blend was prepared as in example 3 of this application, except that Horticultural Perlite (W. R. Grace, Perl-Gro) was substituted for wood flour. The blend was somewhat lumpier, "stickier" and less free flowing than those typically obtained with wood flour. Substantially more lumps over ¼ and even over ½ inch in diameter were formed. This was probably because the Perlite contained relatively few fine particles. However, the blend could be handled and was irradiated at approximately 0.5 megarads. The hydrogel obtained had the following properties:

23.7 water capacity, 82% insoluble.

Sieve analysis of the perlite showed the following results:

| Screen Size | | % of Sample |
|---|---|---|
| retained on 10 mesh | | 0.8% |
| thru 10, not thru 20 mesh | | 36.1% |
| 20 | 30 | 17.1% |
| 30 | 40 | 12.8% |
| 40 | 60 | 15.9% |
| 60 | 70 | 4.4% |
| 70 | — | 13.0% |

EXAMPLE 57

A blend was prepared as in example 1 except that:
1. 2 pounds of POLYOX were used
2. 2 pounds of Matheson Coleman and Bell Co. Reagent Grade Tricalcium Phosphate ($Ca_3(PO_4)_2$) were substituted for wood flour.
3. Approximately 5.7 pounds of water containing 18 grams PEI were used. A small portion was sprayed on the filler, then the PEO was added. Then the remainder of the solution was added.

During the blending, the material was exceptionally free-flowing and free of agglomeration. Almost no agglomerates over ⅛ to 1/8 inch in diameter formed. The blend had a very dry "feel" and did not compact as easily as blends with wood flour.

After irradiation at approximately 0.20, 0.25 and 0.4 Mrad, samples from the blend had these properties:
at 0.2 Mrad, 21.8X water capacity, 61.7% insoluble
at 0.25 Mrad, 21.7X water capacity, 63.7% insoluble
at 0.4 Mrad, 19.7X water capacity, 69.0% insoluble Similar procedure was followed with the following sets of ingredients:
a. 1 pound POLYOX and 1 pound $CaCO_3$, 9 grams PEI in approximately 3.9 pound water.
b. 2 pounds POLYOX, 1 pound dibasic Calcium Phosphate and 1 pound Eastern White Pine wood flour, 18 grams PEI, approximately 5.7 pounds water.
c. 2 pounds POLYOX, 2 pounds gypsum ($CaSO_4.2H_{20}$), 18 grams PEI and approximately 5.7 pounds water.

In none of these three examples was any improvement noted in the physical properties of the blend.

EXAMPLE 58

The procedure of additional example 55 was followed, except that 10% by weight of the wood flour was replaced by an equal weight of technical grade tricalcium phosphate (Matheson Coleman and Bell). Specifically 1.5 pounds POLYOX, 1.35 pounds Eastern White Pine wood flour and 0.15 pounds of calcium phosphate were used, along with 2 liters of water containing 14 grams PEI-1000. Some water was added to the dry blended fillers, then the POLYOX was added. The solids were mixed and water addition continued. After the addition of the normal 2 liters (4.4 pounds) of water, the blend felt "dry", had few lumps greater than ⅛ inch, and flowed unusually freely. A small sample was taken and irradiated at approximately 0.4 Mrad. It had 22X water capacity at 80.5% insoluble fraction.

Because the blending had proceeded well, more water was added. It was possible to add an additional liter of water before agglomeration to lumps ⅛ to ¼ or even ½ inch began to occur. In a blend with wood flour alone, the addition of about 600 more ml. of water causes the blend to agglomerate completely. Thus, the calcium phosphate substantially aided the blending process. A sample of the blend containing 3 liters of water was irradiated at approximately 0.4 Mrad. It had 21× water capacity and 84% insoluble.

The above experiment was repeated, except that only 1% of the wood flour was replaced with sodium phosphate. The improvement in physical properties of the blend was just barely noticeable, although a small amount of lumping and agglomeration occurred. Irradiation of a sample at approximately 0.4 Mrad gave 20×, 81% insoluble material.

On the basis of this experiment, a useful lower limit to blend improvement with calcium phosphate is about 0.5% substitution.

EXAMPLE 59

In an attempt to see if "Cab-O-Sil" or related materials would improve blending, the following experiments were performed. All showed poor results.

Addition of 13.6g of Cab-O-Sil Type 5M5 after 2600ml of water was added in normal blending as in example 3 did not permit the addition of significantly more water without lumping.

A blend was tried with 1.5 pounds PEO, 1.35 pounds wood flour and 0.15 pounds Union Carbide UCAR Sub-Micron Silica. After 2 liters of water were added, the blend was quite lumpy (¼ to ¾ inch agglomerates of 1/32 to 1/16 particles).

EXAMPLE 60

In order to demonstrate the effectiveness of the materials of this invention, diapers were prepared one sixth the normal size: One was prepared containing 7 grams of cellulose wadding as the absorbent. Another was prepared containing 4.15 grams of cellulose wadding and 0.9 grams of the free-flowing polymer prepared from equal amounts of poly(ethylene oxide) and wood flour. Onto each diaper was poured 54 ml of water. At the end of one-half hour excess water was allowed to drip out. The diaper without the polymer failed to absorb 6.8 ml while the one with the polymer failed to absorb 8.5 ml.

Although the invention has been illustrated by the preceding examples, it is not to be construed as being limited to the materials employed therein, but rather, the invention encompasses the generic area as hereinbefore disclosed. Various modifications and embodiments of this invention can be made without departing from the spirit and scope thereof.

What is claimed is:

1. A disposable absorbent article containing a mixture prepared by:

a. blending at least one water soluble pulverulent hydrophilic polymer and at least one pulverulent inert filler in a ratio of polymer to filler of from about 1:9 to about 9:1, a substantial portion of said filler having a particle size less than that of said polymer and present in an amount sufficient to cover a substantial portion of the surface area of said pulverulent polymer.

b. thereafter while said blending is continued, contacting said mixture under thorough agitation with a finely divided spray of water at a rate and in an amount not to exceed that at which the mixture is maintained in a free-flowing particulate form, and c. thereafter exposing said mixture in said free-flowing particulate form to ionizing radiation for a period of time to crosslink said polymer.

2. The disposable absorbent article of claim 1 which is a catamenial device.

3. The disposable absorbent article of claim 1 which is a sanitary napkin.

4. The disposable absorbent article of claim 1 which is a tampon.

5. The disposable absorbent article of claim 1 which is a diaper.

* * * * *